(12) United States Patent
Kim et al.

(10) Patent No.: US 7,303,156 B1
(45) Date of Patent: Dec. 4, 2007

(54) GENERATION AND USAGE OF MICROBUBBLES AS A BLOOD OXYGENATOR

(75) Inventors: Sung Sam Kim, Bossier City, LA (US); Roy Schubert, Simsboro, LA (US)

(73) Assignee: Louisiana Tech University Research Foundation as a Division of the Louisiana Tech University Foundation, Ruston, LA (US)

( * ) Notice: Subject to any disclaimer, the term of this patent is extended or adjusted under 35 U.S.C. 154(b) by 82 days.

(21) Appl. No.: 10/847,718

(22) Filed: May 18, 2004

Related U.S. Application Data

(60) Provisional application No. 60/560,568, filed on Apr. 8, 2004.

(51) Int. Cl.
*B05B 1/04* (2006.01)
(52) U.S. Cl. .................... 239/594; 239/311; 239/369; 239/370; 239/589; 239/592; 422/47; 261/DIG. 28; 604/6.14
(58) Field of Classification Search ............... 239/310, 239/311, 433, 434, 589, 592, 594, 369, 370; 137/268; 222/145.6; 422/45, 47; 261/76, 261/DIG. 28; 604/6.14, 4.01
See application file for complete search history.

(56) References Cited

U.S. PATENT DOCUMENTS

| | | | |
|---|---|---|---|
| 1,826,776 A * | 10/1931 | Gunther ........................ 239/8 |
| 2,724,583 A * | 11/1955 | Targosh et al. ............. 239/311 |
| 3,567,116 A * | 3/1971 | Lindlof ...................... 239/14.2 |
| 4,732,326 A * | 3/1988 | Bessling et al. ............ 239/338 |
| 4,834,343 A | 5/1989 | Boyes |
| 4,846,791 A | 7/1989 | Hattler et al. |
| 4,911,689 A | 3/1990 | Hattler |
| 4,986,809 A | 1/1991 | Hattler |
| 4,993,495 A * | 2/1991 | Burchert ...................... 169/14 |
| 5,073,309 A * | 12/1991 | Bousquet et al. ............. 261/29 |
| 5,122,113 A | 6/1992 | Hattler |
| 5,207,640 A | 5/1993 | Hattler |
| 5,219,326 A | 6/1993 | Hattler |
| 5,271,743 A | 12/1993 | Hattler |
| 5,376,069 A | 12/1994 | Hattler |
| 5,501,663 A | 3/1996 | Hattler et al. |
| 5,869,538 A | 2/1999 | Van Liew et al. |
| 6,127,428 A | 10/2000 | Lundgren et al. |
| 6,237,897 B1 * | 5/2001 | Marina ...................... 261/64.1 |

(Continued)

OTHER PUBLICATIONS

University of Pittsburgh Medical Center Artificial Lung Laboratory. "The IMO Device", www.pitt.edu/~wfedersp/Brochure/IMO.html, downloaded Jun. 25, 2004; believed to have been published as early as Aug. 1997; 3 pgs.; Disclosure Doc. 1.

(Continued)

*Primary Examiner*—Kevin Shaver
*Assistant Examiner*—Jason Boeckmann
(74) *Attorney, Agent, or Firm*—Jones, Walker, Waechter, Poitevent, Carrere, & Denegre, L.L.P.

(57) ABSTRACT

A micro-nozzle for generating micro-bubbles. The micro-nozzle includes a liquid inlet forming a liquid path, a gas inlet, and a constricting wall positioned in the liquid path and shaped to abruptly constrict said liquid path to a width of less than approximately 20 um and then gradually diverge.

23 Claims, 5 Drawing Sheets

U.S. PATENT DOCUMENTS

| | | |
|---|---|---|
| 6,241,897 B1 * | 6/2001 | Hanson et al. .............. 210/739 |
| 6,328,898 B1 | 12/2001 | Akiyama et al. |
| 6,334,705 B1 | 1/2002 | Weetman |
| 6,382,601 B1 | 5/2002 | Ohnari |
| 6,511,054 B1 | 1/2003 | Green |
| 6,537,246 B1 | 3/2003 | Unger et al. |
| 2004/0009096 A1 * | 1/2004 | Wellman .................... 422/44 |

OTHER PUBLICATIONS

Dissertation by Sung Sam King entitled "Generation of Oxygen Microbubbles in a Microchannel with Crosscurrent Liquid Flow", Louisiana Tech University, May 2001 132 pgs.; Disclosure Doc. 2.

Article by R.W. Schubert, S.A. Conrad and S.S. Kim entitled "Using Microbubbles to Oxygenate Blood: Possible?", Ruston, Louisiana; Sep. 2003; 4 pgs.; Disclosure Doc. 3.

Thesis by Paul Jerome Unkel entitled "The Study of Oxygen Transport from Micro-Bubbles in 0.9% Saline," Louisiana Tech University, Nov. 1991; 75 pgs.; Disclosure Doc. 4.

Thesis by Ashok Krishnan entitled "Intravascular Microbubble Blood Oxygenator: Principles & Limitations," Louisiana Tech University, Nov. 1994; 88 pgs.; Disclosure Doc. 5.

University of Pittsburgh Medical Center Artificial Lung Laboratory, http://info.pitt.edu/~wfedersp/alhtml.htm, downloaded Aug. 31, 2004; believed to have been published as early as Aug. 1997; 2 pgs.; Disclosure Doc. 6.

* cited by examiner

AA SECTION

BB SECTION

CC SECTION

GENERATION AND USAGE OF MICROBUBBLES AS A BLOOD OXYGENATOR

CROSS-REFERENCE TO RELATED APPLICATION

This application claims the benefit under 35 USC 119(e) to U.S. Provisional Application No. 60/560,568, filed Apr. 8, 2004, which is incorporated by reference herein in its entirety.

STATEMENT REGARDING FEDERAL SPONSORED RESEARCH

N/A

BACKGROUND OF INVENTION

The present invention relates to devices, particularly nozzles, for producing very fine bubbles of gas in a liquid medium.

There are many uses for the production of very fine gas bubbles in a liquid medium. One such use is for the mechanical oxygenation of blood (as opposed to oxygenation by lungs or other biological processes). It is important for blood oxygenation devices that bubble size be sufficiently small and consistently be at or below the required size. Additionally, it is advantageous if the oxygenation device is sufficiently small that it can be inserted into the larger human veins.

SUMMARY OF INVENTION

The present invention provides a micro-nozzle for generating micro-bubbles. The micro-nozzle includes a liquid inlet forming a liquid path, a gas inlet, and a constricting wall positioned in the liquid path and shaped to abruptly constrict said liquid path to a width of less than approximately 20 um and then gradually diverge.

The present invention also includes a device for the generation of micro-bubbles. The device includes a device body and a plurality of micro-nozzles formed on the device body. The plurality of micro-nozzles have a liquid inlet forming a liquid path, a gas inlet, and a constricting wall positioned in the liquid path and shaped to abruptly constrict the liquid path to a width of less than approximately 20 um and then gradually diverge. Liquid and gas passages communicate through the device body with the liquid and gas inlets of the micro-nozzles.

DETAILED DESCRIPTION OF INVENTION

Figure 1:
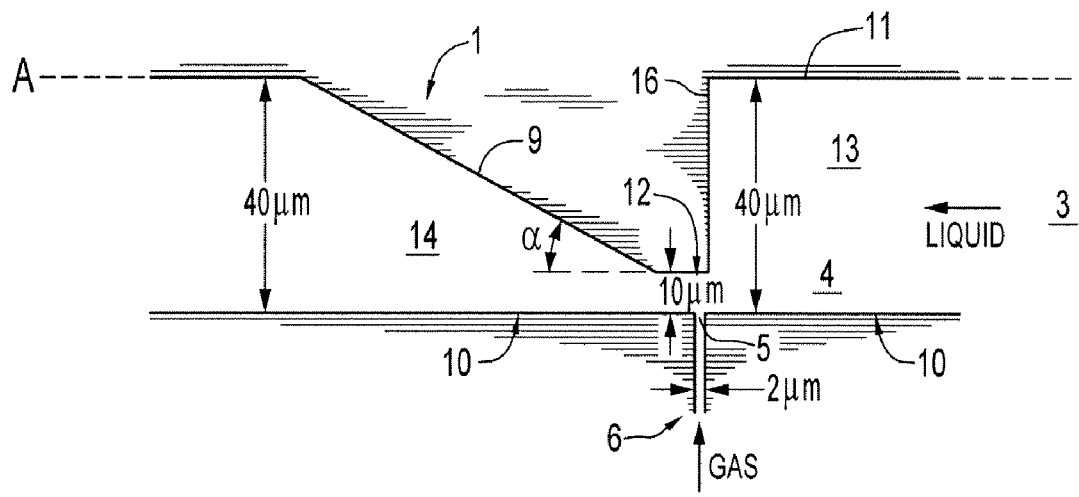
FIG. 1 is a top view of one embodiment of the micro-nozzle of the present invention.

The primary element of the micro-bubble generating device of the present invention is a novel micro-nozzle. FIG. 1 illustrates one embodiment of the micro-nozzle 1 of the present invention. Micro-nozzle 1 will typically have a liquid inlet 3 which forms a liquid path 4 between bottom wall 10 and top wall 11. In the embodiment of FIG. 1, top and bottom walls 11 and 10 are shown as shaded areas whereas the channel formed by liquid inlet 3 and liquid path 4 is unmarked. In the embodiment shown, the depth of this channel (i.e. the dimension perpendicular to the plane in which FIG. 1 is drawn) may be approximately 10 um. Liquid path 4 generally flows undisturbed through the unconstricted region 13 until it approaches constriction point 12. Unconstricted area 13 is "unconstricted" in the sense that is it substantially more open than constriction point 12 and generally conducive to uniform flow characteristics. For example, in the embodiment of FIG. 1, unconstricted area 13 is an uniform channel approximately 40 um wide. However, it may be advantageous to make unconstricted area 13 as wide as possible considering the overall nozzle size constraints. Unconstricted region 13 abruptly ends as the liquid path 4 encounters downward extending front wall or constricting wall 16 which extends downward to constriction point 12. The actual width of the liquid path at constriction point 12 may vary. It is believed that there is a general correlation between the width of constriction point 12 and the size of the micro-bubble which exits micro-nozzle 1. In order to produce micro-bubbles that are approximately 20 um or less in diameter, it is preferred that constriction point 12 should be no greater than approximately 20 um. Likewise, to produce micro-bubbles that are approximately 10 um or less in diameter, it is preferred that constriction point 12 should be no greater than approximately 10 um.

A gas path 6 will join liquid path 4 at gas inlet 5. While not necessarily critical to all embodiments, a preferred embodiment of micro-nozzle 1 will position gas inlet 5 approximately at constriction point 12 and even more preferably at the beginning of constriction point 12. The "beginning" of constriction point 12 is where fluid path 4 suddenly constricts from the unconstricted area 13. In the embodiment of FIG. 1 where constriction point 12 is 10 um, fluid inlet 3 width is approximately 40 um and gas inlet 5 is approximately 2 um.

As fluid path 4 continues past constriction point 12, it enters divergent region 14. Divergent region 14 is formed by diverging wall 9 inclining away from bottom wall 10. The rate at which diverging wall 9 diverges may vary in different embodiments, but in one preferred embodiment, the angle "alpha" that diverging wall 9 makes relative to bottom wall 10 is less than about 45°. In a more preferred embodiment, angle alpha is 12° or less in order to promote laminar flow. In a preferred embodiment, divergent region 14 will extend for approximately 500 um or more beyond constriction point 12.

Figure 2:
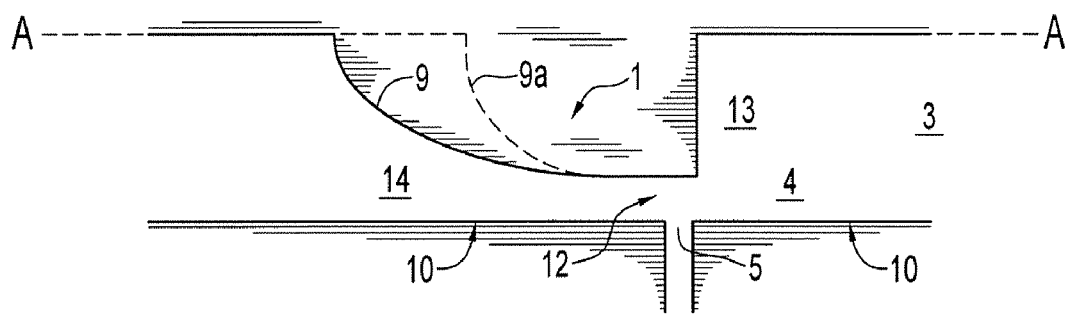
FIG. 2 is a top view of another embodiment of the micro-nozzle of the present invention.

FIG. 2 illustrates an alternative embodiment of micronozzle 1. Here a diverging wall 9 takes a parabolic shape in the divergent region 14. This parabolic shape in essence allows diverging wall 9 to smoothly transition from a divergence angel of 0° to 90°. As in FIG. 1, this embodiment positions gas inlet 5 at the beginning of constriction point 12 and sizes constriction point 12 and gas inlet 5 at 10 um and 2 um respectively. The gas inlet location is in a region where the Bernoulli equation suggest the lowest side-arm (static) pressure, e.g. the narrowest point of the constriction. Naturally, diverging wall 9 may take many different shapes. Alternative embodiments could include a semicircular constricting wall as suggested by dashed line 9a.

Figure 1A:
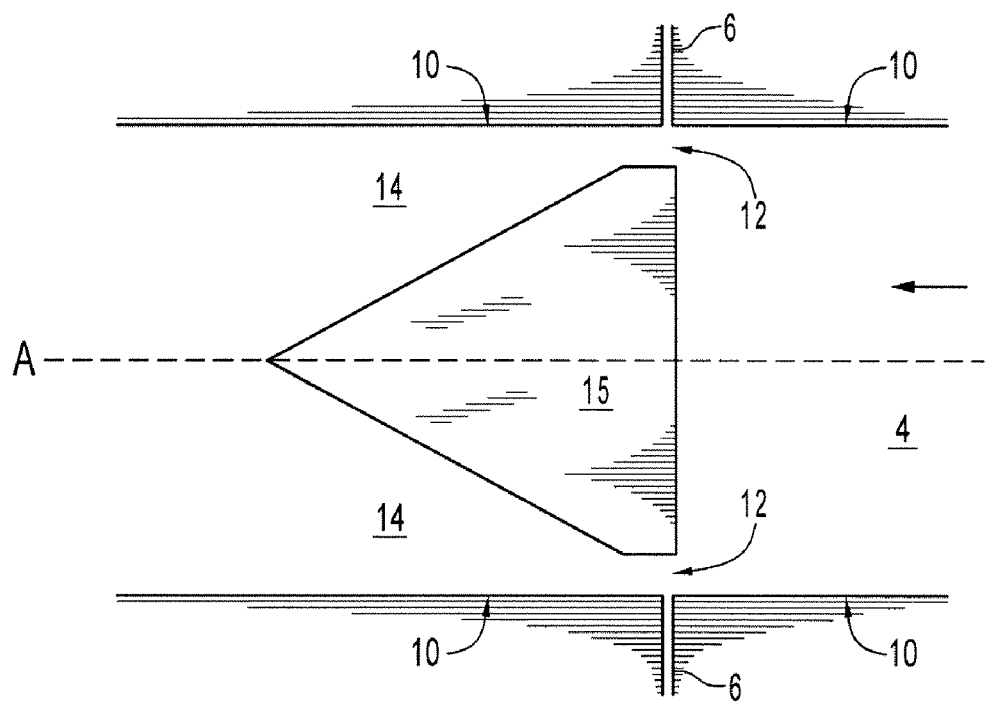
FIG. 1A illustrates the micro-nozzle embodiment of FIG. 1, but formed with a symmetrical island structure.
Figure 3:
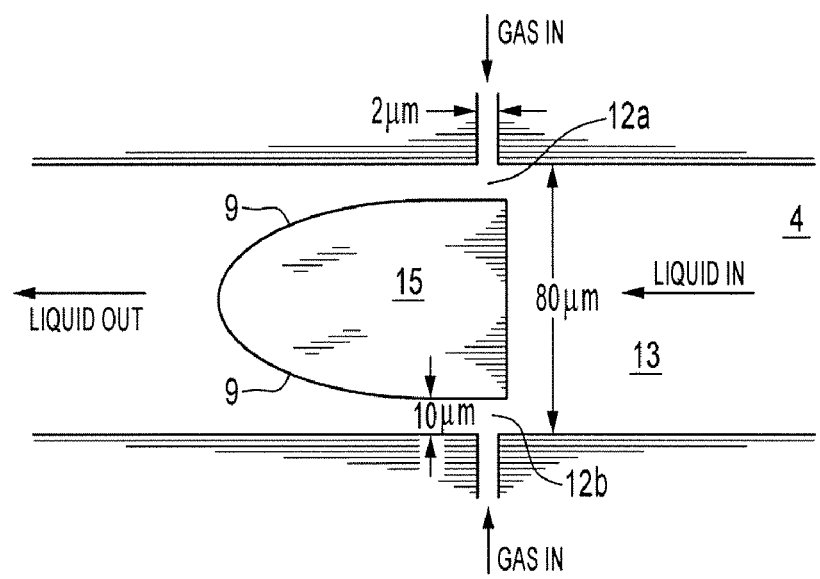
FIG. 3 illustrates the micro-nozzle embodiment of FIG. 2, but formed with a symmetrical island structure.

FIG. 3 shows a compact double nozzle arrangement which comprises FIG. 2 and its mirror image along the centerline A. Here dual diverging walls 9 are formed by island structure 15 in liquid path 4, which in the embodiment shown is approximately 80 um in width (i.e. the liquid path 4). It can be seen that diverging walls 9 take a parabolic shape to form two constriction points 12a and 12b. This symmetrical compact pattern lends itself to efficient replication on a large scale as shown below. Naturally those skilled in the art will recognize many variations of micro nozzles 1 seen in FIGS. 1-3 and all such variations are within the scope of the present invention. For example, FIG. 1A illustrates an island structure formed of a pair of linear diverging walls such as seen in FIG. 1.

The rate at which fluid and gas are supplied to micronozzle 1 may also influence the size of bubbles generated. For example, with a micro-nozzle having the dimensions given relative to FIGS. 1 and 2, it is preferred to maintain a gas flow rate below approximately 1 uL/min and a fluid a fluid velocity of at least 0.33 m/sec. In one preferred embodiment, both the gas and fluid will be supplied at a pressure of approximately 2 p.s.i. It is also believed that employing saline as the liquid component facilitates smaller bubbles based on surface tension data. When the gas component is oxygen and the liquid is an oxygen saturated saline solution the bubble tends to remain filled with oxygen rather than experiencing an inrush of nitrogen.

Figure 4:
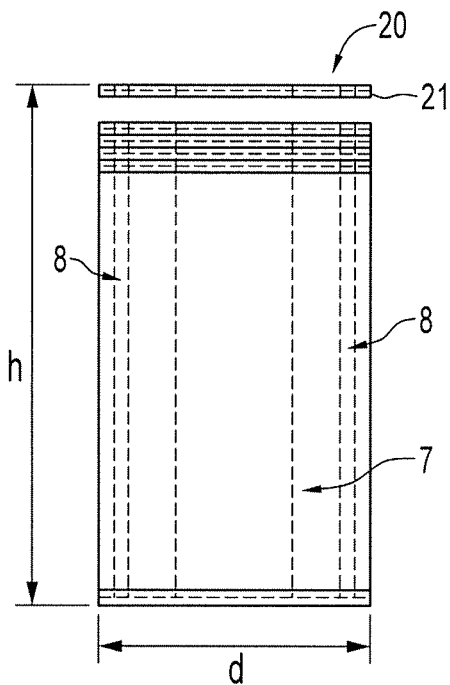
FIG. 4 is a side view of one embodiment of a micro-bubble generating device constructed of multiple nozzle disks.
Figure 5:
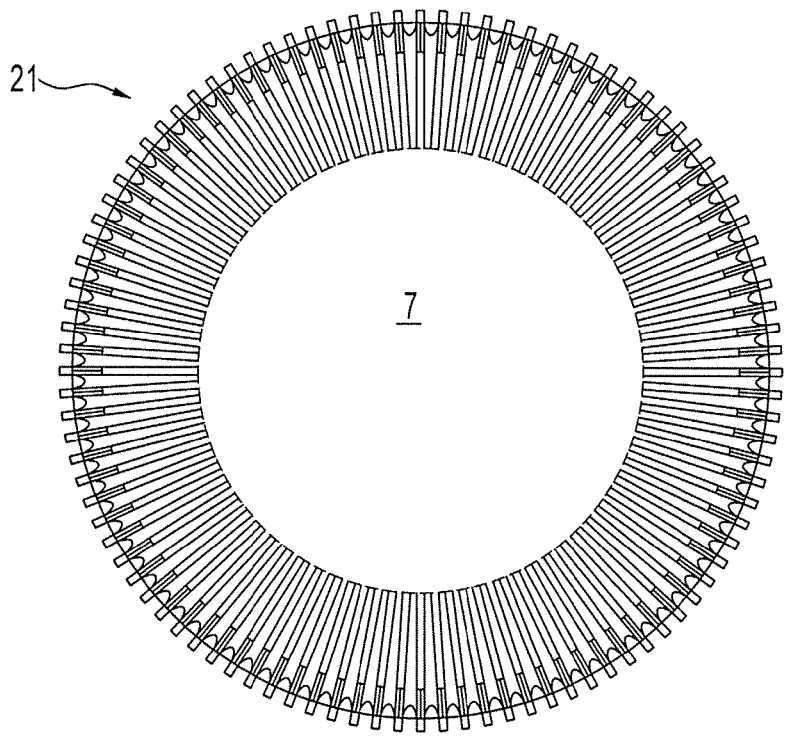
FIG. 5 is a top view of a nozzle disk seen in FIG. 4.
Figure 6A:
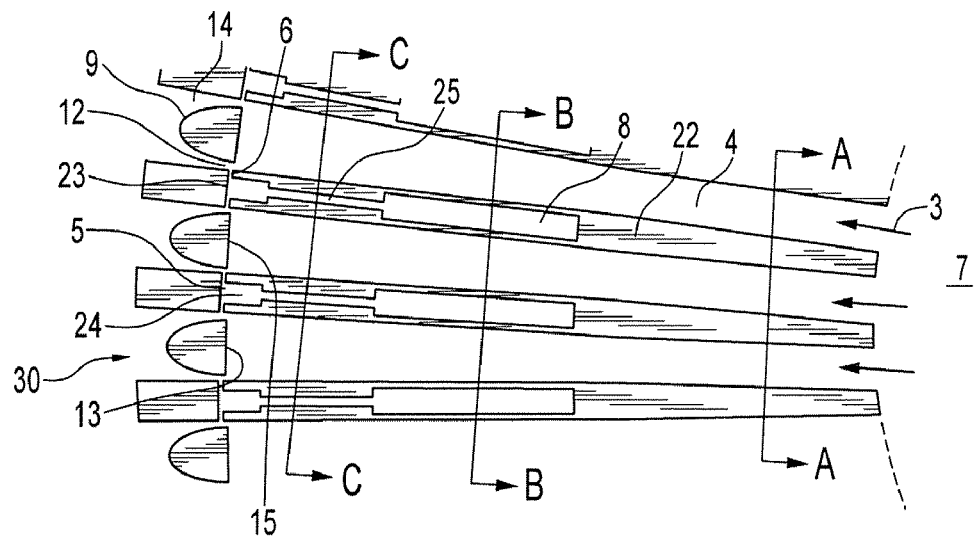
FIG. 6A is a top view of an enlarged section of a nozzle disk containing multiple micro-nozzles similar to that seen in FIG. 3.
Figure 6B:
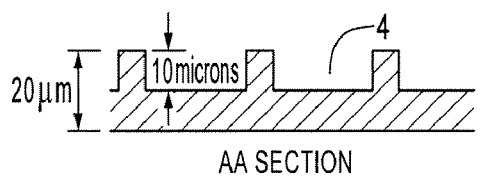
FIGS. 6B, 6C and 6D are sectional views of the nozzle disk seen in 6A.

Another aspect of the present invention is a device for generating micro-bubbles which incorporates micro-nozzle 1. In one embodiment, the micro-bubble generator 20 will take a cylindrical shape and will be formed of a series of nozzle disks 21 stacked atop one another as suggested in FIG. 4. Each nozzle disk 21 will contain a plurality of nozzles 1 as seen in FIG. 5 and will include a center opening which forms a liquid passage 7. FIG. 4 suggests how a continuous liquid passage 7 will be formed when a series of nozzle disks 21 are stacked atop one another. FIGS. 6A-6D better illustrate the details of how nozzles 1 will be formed on nozzle disk 21. FIG. 6A shows an enlarged view of one arc or section of nozzle disk 21 which includes several nozzles 1. Liquid paths 4 will be formed on disk 21 with divider wall structures 22 being left between adjacent liquid paths 4. Each liquid path 4 will originate at and communicate with liquid passage 7. The opposite end of each liquid path 4 will contain an island structure 15 forming two micro-nozzles 1 in the same manner as described in reference to FIG. 3.

Figure 6C:
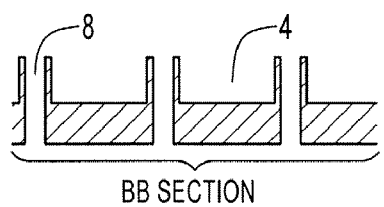
Figure 6D:
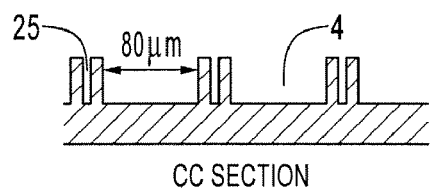
Figure 6E:
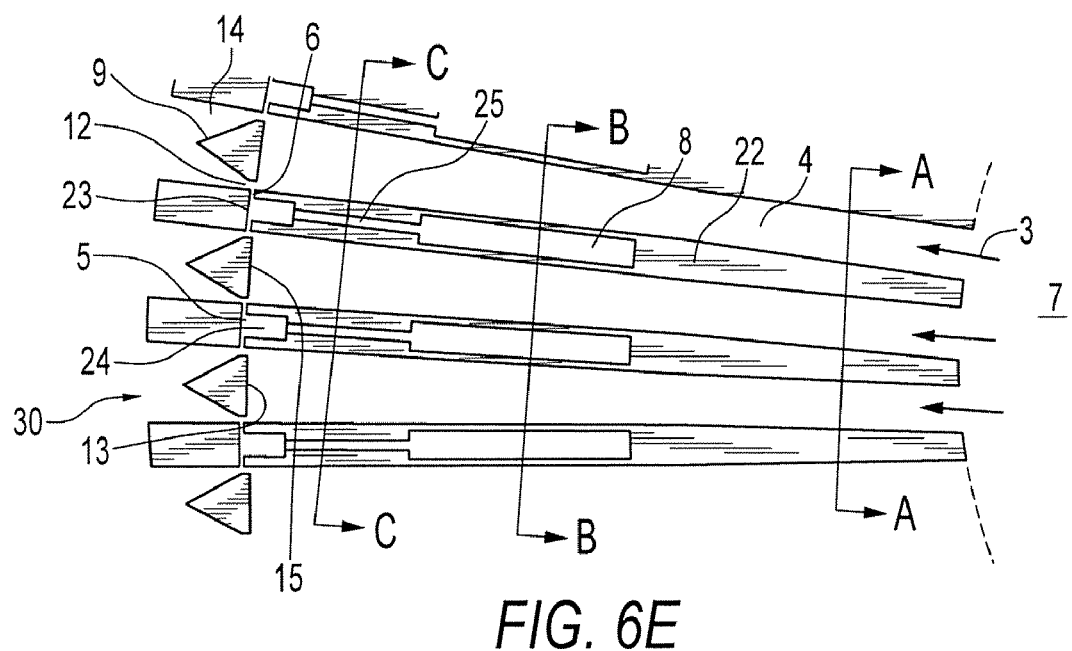
FIG. 6E is a top view of an enlarged section of a nozzle disk containing multiple micro-nozzles similar to that seen in FIG. 1A.

Within each divider wall 22, there will be a gas passage 8 formed through disk 21 and communicating with a restricted gas path 25 running down the upper half of divider wall 22. Again viewing FIG. 4, it can be seen how gas passage 8 is a continuous channel through bubble generating device 20 when nozzle disks 21 are stacked. In the preferred embodiment seen in FIG. 6A, it is shown how the restricted gas path 25 opens up to an enlarged chamber 24 which terminates at end walls 23. However, a small cut running parallel to endwall 23 will separate divider walls 22 from end walls 23 and will form gas inlets 5 on each side of divider wall 22. It is believed that the transition from restricted gas path 25 to the more open chambers 24, together with the compressibility of the gas and resistance in restricted path 25, induces an oscillatory effect which assists in the creation of discrete bubbles. In one preferred embodiment, nozzle disks 21 could be formed of poly methyl methacrylate (PMMA). Such PMMA nozzle disks 21 could be made through a conventional molding/stamping process such as disclosed in *Fundamentally of Microfabrication*, Marc Madou, CRC Press, 1997, Chapter 6, which is incorporated by reference herein. FIG. 6C illustrates cross-section BB and how gas passages 8 will be formed through nozzle disk 21 between adjacent liquid paths 4. It will be apparent from FIG. 4 how the bottom of each nozzle disk 21 acts as a cover for the nozzle disk 21 below it. It can further be understood that when the nozzle disks 21 are in a stacked configuration such as shown in FIG. 4, the individual nozzle outlets 30 (see FIG. 6A) will be formed on (i.e., open onto) the outer surface of the cylindrical body of micro-bubble generator 20. FIG. 6D illustrates how the gas path is restricted in the area of path 25. The cross-section CC of FIG. 6D and AA of FIG. 6B suggest how the embodiment shown would have liquid paths 4 approximately 10 μm deep, with a 80 μm width similar to that shown in FIG. 3, and an overall disk thickness of 20-30 μm. Alternatively, FIG. 6E illustrates a structure similar to 6A, but the island structure 15 is constructed in accordance with FIGS. 1 and 1A as opposed to FIGS. 2 and 3.

In the embodiment of FIGS. 4-6, nozzle disk 21 could be a plastic wafer or washer type structure with the various channels and structures creating micro-nozzles 2 being formed by conventional lithographical methods. Of course, nozzle disks 21 could be formed of any other material and any other machining technique which allowed the creation of the micro-nozzles 1. Alignment of adjacent nozzle disks could be accomplished by placing an alignment tab or notch on the disks on the liquid inflow side (not shown in the figures) and using an jig for assembly.

The number of double micro-nozzles 1 on each nozzle disk 21 and the number of nozzle disks 21 stacked to form the bubble generation device 20 could vary greatly depending on various design parameters. As one illustrative example, if bubble generation device 20 is intended to oxygenate blood by being placed in a human vein, it may be considered that a 70 kg human at rest requires approximately 250 ml/min of oxygen (at 1 atmosphere pressure and 23° C.). It is calculated from the geometry that the STP gas volume of a 5 um radius bubble is $6.683 \times 10^{-9}$ ml, considering the surface tension. It is also believed that double micro-nozzle 1 embodiment shown in FIG. 3 is capable of generating approximately 10,000 bubbles per second, thus requiring approximately $6.235 \times 10^5$ double micro-nozzles to meet the required oxygenation rate. A nozzle disk 21 approximately 0.25 inches in diameter is capable of containing approximately 90 double micro-nozzles around its perimeter, thus, $6.982 \times 10^3$ nozzle disks would be required. If each nozzle disk 21 is approximately 20 um thick, the overall bubble generating device 20 such as seen in FIG. 4 will have a height "h" of approximately 5.45 inches. Alternatively, if designing for 15 um bubbles, then the device height may be reduced allowing the use of thicker, sturdier nozzle disks. For example, designing for 15 um bubbles and using thirty micron thick nozzle disks would allow construction of a micro-bubble generating device with a height of approximately 2.6 inches in length.

Although the present invention has been described in terms of specific embodiments, those skilled in the art will recognize many obvious variations and modifications. All such variations and modifications are intended to come within the scope of the following claims.

The invention claimed is:

1. A micro-nozzle for generating micro-bubbles comprising:
   a. a liquid inlet forming a liquid path;
   b. a constricting wall positioned in said liquid path and shaped to constrict said liquid path to a constriction point of less than approximately 20 microns;
   c. a gas inlet positioned at approximately the beginning of said constriction in the liquid path;
   d. a divergence region immediately following said constriction point, said divergence region comprising a diverging wall extending away from said constriction point and opposite said diverging wall, a parallel wall extending away from said constriction point parallel to said liquid path.

2. The micro-nozzle of claim 1, wherein said liquid path is constricted to a width less than approximately 15 microns.

3. The micro-nozzle of claim 1, wherein said liquid path is constricted to a width less than approximately 10 microns.

4. The micro-nozzle of claim 1, wherein said liquid path includes an outlet which gradually opens into said divergence region.

5. The micro-nozzle of claim 1, wherein said diverging wall diverges in a substantially straight line with a slope of less than 45°.

6. The micro-nozzle of claim 1, wherein fluid flows through said constricted liquid path at a velocity of approximately 0.33 meters per second and gas flows through said gas inlet at a rate of approximately 1 micro-liter per second.

7. The micro-nozzle of claim 5, wherein said slope is approximately 12°.

8. The micro-nozzle of claim 1, wherein said micro-nozzle is formed in a PMMA material.

9. The micro-nozzle of claim 1, wherein said gas inlet is preceded by a gas path that comprises a restricted section and a more open section.

10. The micro-nozzle of claim 1, wherein said constricting wall is perpendicular to said liquid path.

11. The micro-nozzle of claim 1, wherein said liquid path is abruptly constricted to said approximately 20 microns.

12. The micro-nozzle of claim 1, wherein air bubbles produced by said micro-nozzle are less than approximately 20 microns in diameter.

13. The micro-nozzle of claim 1, wherein gas is supplied to said gas inlet at a positive pressure.

14. A nozzle disk comprising a series of micro-nozzles formed around the perimeter of a disk, said micro-nozzles each comprising:
   a. a liquid inlet forming a liquid path, said liquid path including a first wall generally parallel to said liquid path;
   b. a gas inlet;
   c. a constricting wall positioned in said liquid path and shaped to constrict said liquid path to a constriction point of less than approximately 20 microns; and
   d. a divergence region following said constriction point and being formed by a diverging wall extending away from said constriction point and inclining away from said first wall at an angle of less than about 45 degrees.

15. The nozzle disk of claim 14, wherein said liquid path and said gas inlet are on a horizontal plane of said nozzle disk.

16. The nozzle disk of claim 14, wherein said gas inlet of said micro-nozzles is preceded by a gas path that comprises a restricted section and a more open section.

17. A device for the generation of micro-bubbles comprising:
   a. a device body;
   b. a plurality of micro-nozzles formed on said device body;
   c. said plurality of micro-nozzles comprising: i) a liquid inlet forming a liquid path, ii) a constricting wall positioned in said liquid path and shaped to abruptly constrict said liquid path to a width of less than approximately 20 microns, and iii) a gas inlet positioned at approximately the beginning of said constriction in said liquid path; and
   d. liquid and gas passages communicating through said body with said liquid and gas inlets of said micro-nozzles.

18. The device of claim 17, wherein said body is substantially cylindrical.

19. The device of claim 17, wherein said micro-nozzles have outlets formed on a surface of said body.

20. The device of claim 17, wherein a divergence region follows said constricting wall.

21. The device of claim 17, wherein said liquid path is generally parallel before and after said gas inlet.

22. The device of claim 17, wherein said micro-nozzles include a restricted path followed by a more open chamber.

23. The device of claim 17, wherein in said body is formed from a plurality of planer segments and a plurality of micro-nozzles are formed on each of said planar segments.

* * * * *